United States Patent [19]

Seidenberg

[11] Patent Number: 4,887,286
[45] Date of Patent: Dec. 12, 1989

[54] X-RAY POSITIONING AID

[76] Inventor: Jack W. Seidenberg, 936 Madison Ave., Woodmere, N.Y. 11598

[21] Appl. No.: 217,190

[22] Filed: Jul. 11, 1988

[51] Int. Cl.⁴ .............................................. G03B 42/02
[52] U.S. Cl. ..................................... 378/170; 378/206
[58] Field of Search ................................ 378/206, 170

[56] References Cited

U.S. PATENT DOCUMENTS

| 2,659,824 | 11/1953 | Burnham . | |
| 3,628,021 | 12/1971 | MacDonald | 378/206 |
| 3,831,031 | 8/1974 | Barrett et al. . | |
| 4,012,638 | 3/1977 | Altschuler et al. | 378/206 |
| 4,100,408 | 7/1978 | Marshall . | |
| 4,428,029 | 1/1984 | Baliozian . | |

Primary Examiner—Craig E. Church
Attorney, Agent, or Firm—Wolder, Gross & Yavner

[57] ABSTRACT

An apparatus for assisting in the positioning of a dental X-ray generating unit for the creation of an X-ray image of an internal target portion of the mouth separated from the X-ray generating unit by a soft-tissue facial portion is composed of a substantially X-ray-transparent body adapted to be mounted in the path of the X-rays between the X-ray generating unti and the film element and an illumination source mounted to the body. The body has an outwardly-directed face positioned essentially perpendicular to the X-ray path and facing the soft-tissue facial portion between the X-ray source and target. The illumination source is positioned to direct at least one beam of light perpendicular to and outwardly from the body face towards the facial feature along the path of the X-rays generated by the generating unit to produce at least one light spot on the facial feature to serve as an orientation means for said X-ray unit. The apparatus may be dimensioned for positioning either within the mouth or affixed to the X-ray generator.

8 Claims, 3 Drawing Sheets

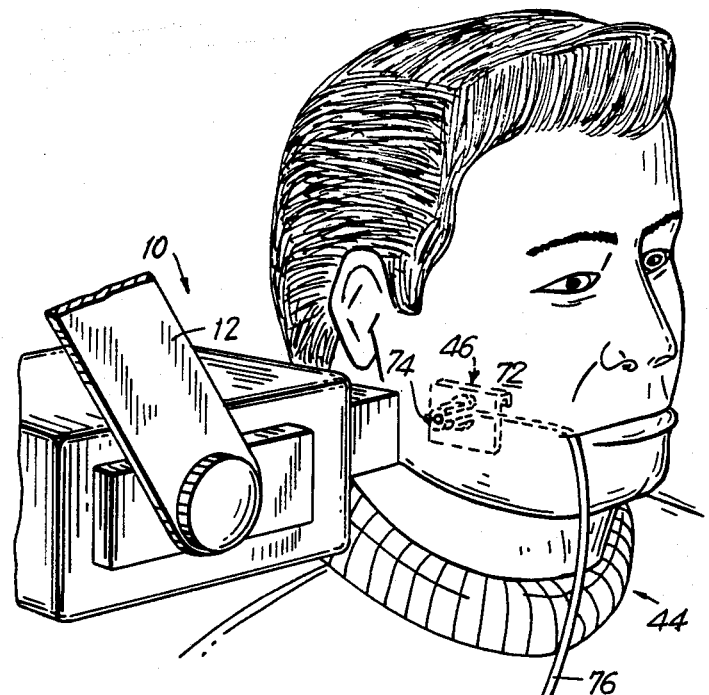
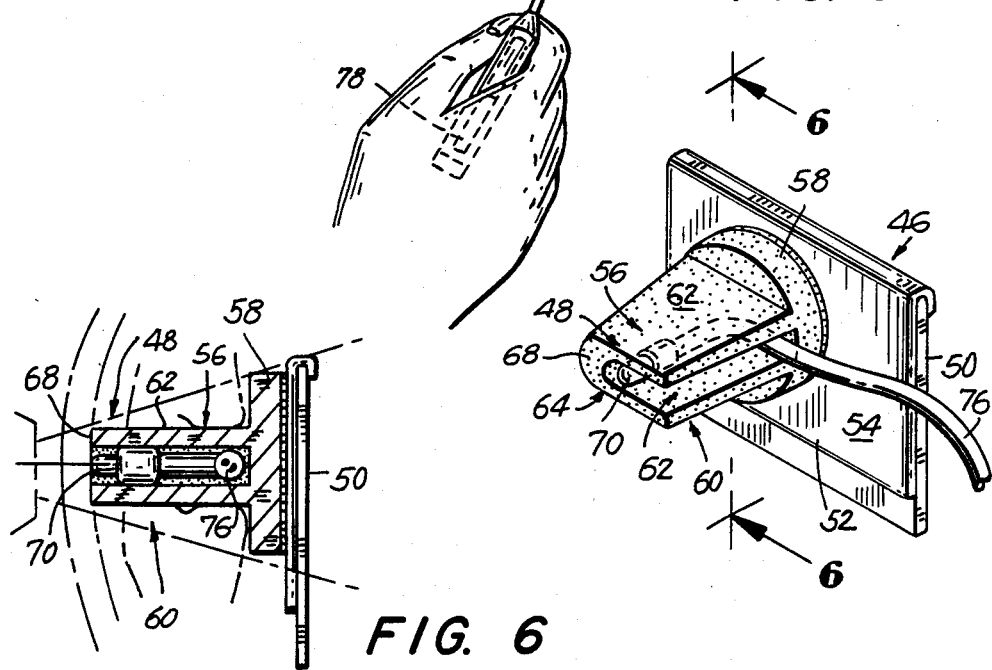

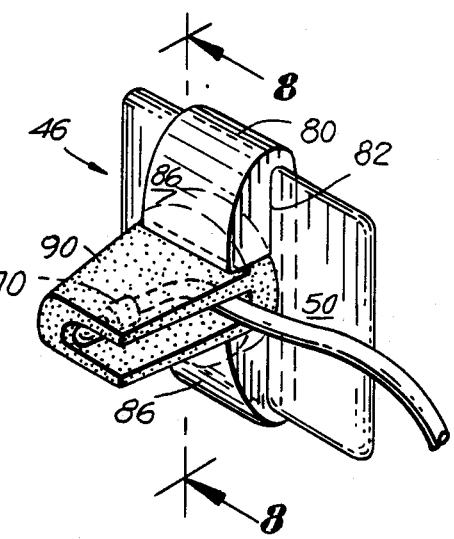
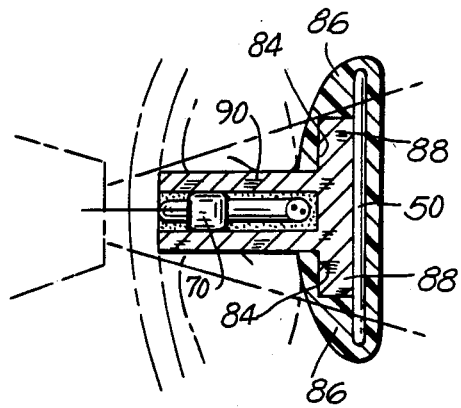
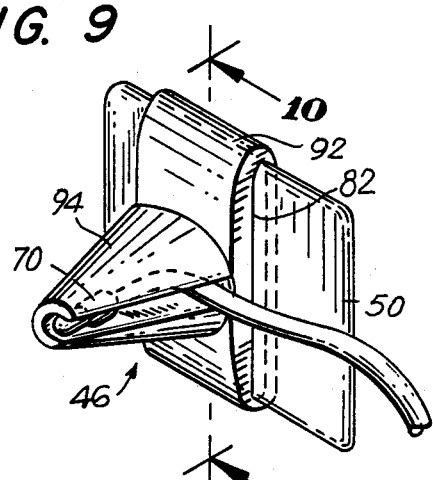
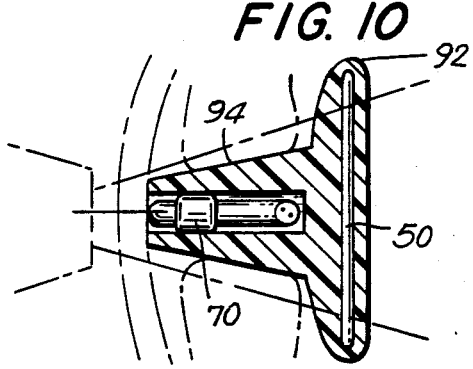
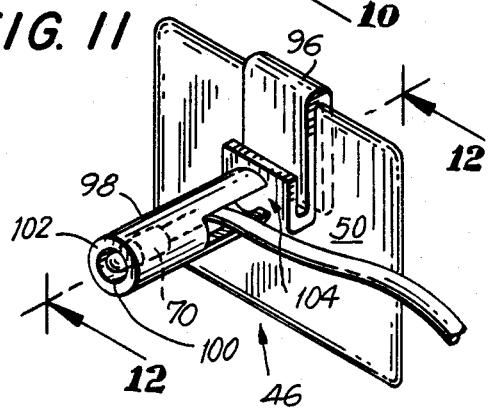
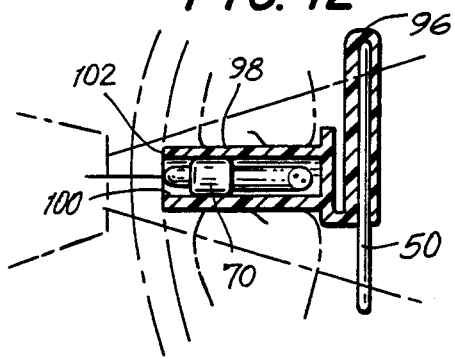

X-RAY POSITIONING AID

The present invention relates to the dental arts and, in particular, to a new and improved device to assist in the positioning of an X-ray apparatus with respect to a patient to allow accurate creation of a desired X-ray image.

The use of X-ray equipment to diagnose and detect dental abnormalities is well-known and highly developed. In general, an X-ray operator, which may be a dentist or a trained and supervised X-ray operator, locates an X-ray generator apparatus proximate the portion of the patient's face overlying the dental area sought to be observed, and positions a film element within the patient's mouth, on the interior side of the area of interest. Normally, the film element is maintained in position by the clamping of the patient's teeth on a portion of a specially designed film holder. Relying upon the skill and experience of the practitioner, the X-ray unit must be properly positioned to generate an X-ray beam which passes through the area of interest and which strikes the film sheet to provide the latent image to be developed. Notwithstanding the practitioner's skill, however, X-ray images are often off center or fail to completely cover the area of interest, due to mispositioning of the X-ray source. This can require additional X-rays to be taken, thus subjecting the patient to greater X-ray dosages, and additionally is wasteful of equipment and operator time, as well as film.

It is accordingly a purpose of the present invention to provide an X-ray source positioning aid which allows the X-ray operator to more clearly locate the area of the patient's mouth to be within the X-ray projection zone.

Yet another purpose of the present invention is to provide such an apparatus which may be easily utilized by the practitioner, and which is not invasive or in any way harmful to the health of the patient.

In accordance with the above and other objects, the present invention comprises an apparatus having a body portion which is positioned within the path of X-ray emission. The body has a face which is located essentially perpendicular to the X-ray path. One or more light-generating means are located on the face, such that they emit light parallel to the X-ray path. Such beams are projected upon the soft tissue of the mouth between the X-ray source and dental area sought to be X-rayed, and thus locate the X-ray path so that appropriate adjustment and correction in the path can be made if required.

In a first embodiment, the body of the apparatus is removably inserted upon the nose cone of the X-ray source, and projects the light images upon the skin surface of the patient at locations which define the extremities of the X-ray beam. In a second embodiment, the light generating means are provided on an apparatus body which may be placed in the patient's mouth and positioned identically to the positioning of the film sheet to be used during the X-ray procedure. The light projection means project a beam against the inner surface of the cheek. Because of the fleshy composition of the cheek, an image may be seen on the cheek exterior, thus allowing positioning of the X-ray head member.

A fuller understanding of the present invention may be achieved upon consideration of the following detailed description of preferred, but nonetheless illustrative embodiments thereof taken in conjunction with the annexed figures, wherein FIG. 1 is a perspective view of an X-ray apparatus with a first embodiment of the invention placed thereon in position with respect to a patient;

FIG. 4 is a perspective view of a second embodiment of the invention in which the body of the apparatus is supported within the mouth of the patient;

FIG. 5 is an enlarged perspective view of the body of the second embodiment of the invention;

FIG. 6 is a side elevational view, in section, taken along line 6—6 of FIG. 5;

FIG. 7 is a first alternative of the second embodiment of the invention;

FIG. 8 is a side elevational view, in section, of the form of the invention shown in FIG. 7, taken along line 8—8 therein;

FIG. 9 is a perspective view of a second alternative embodiment of the second form of the invention;

FIG. 10 is a side elevational view, in section, of the form of the invention shown in FIG. 9, taken along line 10—10 therein;

Figure 1:
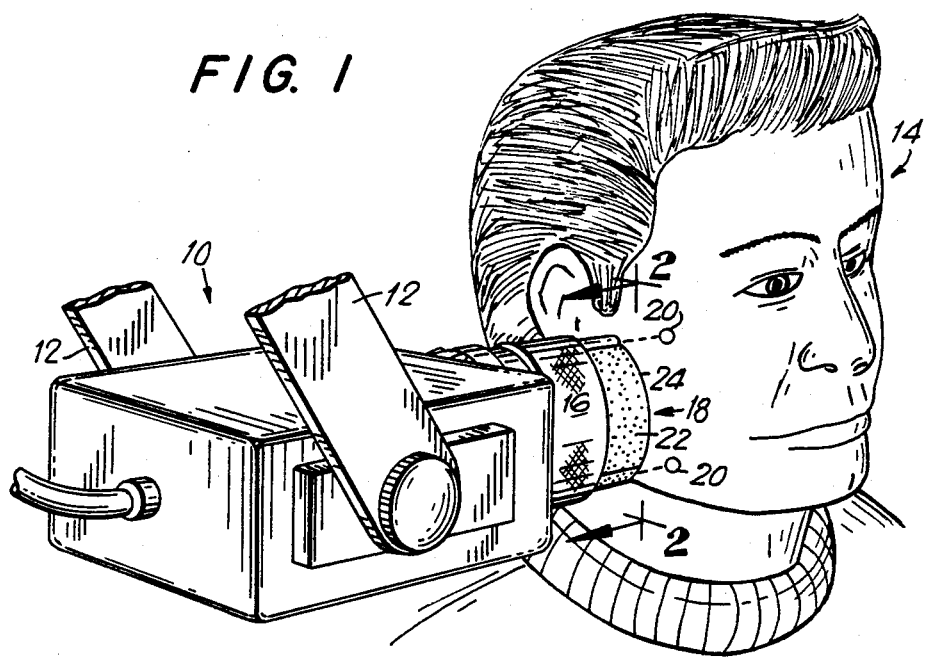
Figure 2:
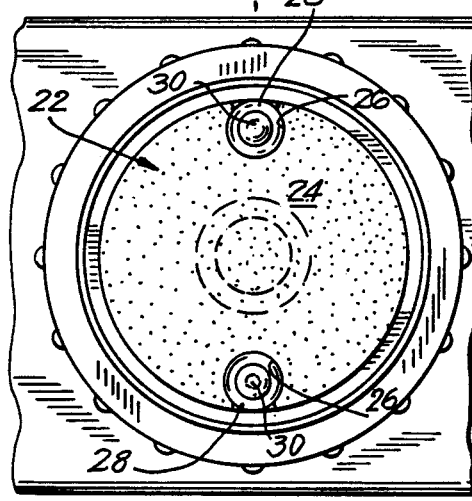
FIG. 2 is a front elevation view of the invention in place on the X-ray head as seen along line 2—2 of FIG. 1.
Figure 3:
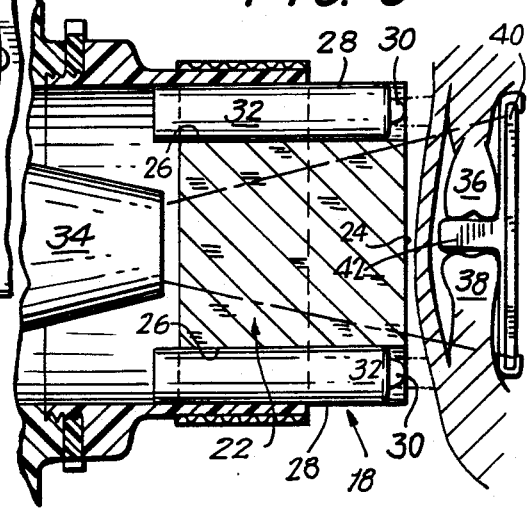
FIG. 3 is a side elevational view, in section, taken along line 3—3 of FIG. 2 further showing the positioning of the X-ray head and the present invention with respect to an X-ray film holder being maintained in position by the patient's teeth.

FIG. 11 is a perspective view of a third alternative embodiment for the second embodiment of the invention; and FIG. 12 is a side elevational view, in section, of the form of the invention shown in FIG. 11, taken along line 12—12 therein. Referring initially to the embodiment shown in FIGS. 1 through 3, a dental X-ray unit having an X-ray generating head 10 pivotly mounted to support arms 12 is positioned adjacent a patient 14 such that the X-ray emitting nose cone 16 of the generating head is directed in the conventional manner towards the portion of the patient's face overlying that portion of the dental structure sought to be X-rayed. X-ray alignment device 18 of the present invention is mounted to the forward open end of nose cone 16, and projects a pair of illuminated spots 20 upon the skin of the patient, thus indicating the width of the X-ray field.

In particular, unit 18 includes a main body portion 22 formed of a rigid yet compliant material, such as cork, chosen to offer little barrier to the passage of X-rays therethrough. The body is dimensioned to fit snugly within the nose cone 16. When in position, front face 24 is perpendicular to the major axis of X-ray emission. Mounted in a pair of diametrically opposed recesses 26 are a pair of light-emitting units 28, each of which may comprise a light-emitting element 30, which may be in the form of a light bulb, as well as a source of energy for the bulbs, as exemplified by batteries 32. The bulbs 30 and batteries 32 may be joined together by a suitable housing, as well known in the art, which may include switch means for engaging and disengaging the units.

The light-emitting units 28 are so oriented that each projects a beam of light outwardly from the front face 24 of main body 22 parallel to the major axis of X-ray emission, such that light spots 20 are projected upon the skin of the patient. To insure that the spots 20 are sharp and clear, pre-focused bulbs, which include an integral lens, may be used. X-ray head 10 may then be positioned as required to allow the X-ray beam generated by emitting element 34 to pass through the portion of the face of the patient between the illumination spots 20 such that the desired portion of the patient's dental features, such as upper and lower teeth 36, 38, and their supporting bone structure, are imaged on conventional X-ray film element 40, which is supported in X-ray-transparent holder 42 which is grasped and positioned by the teeth of the patient as known in the art.

As body 22 is chosen to be essentially X-ray-transparent, the mounting of locating apparatus 18 in the path of X-ray emission does not negatively impact upon film exposure. While batteries 30 and bulbs 28 are not significantly X-ray-transparent, their locations about the periphery of the body 22, position them such that they do not constitute a significant impediment to X-ray passage through the unit, as can be best seen in FIG. 3. Alternatively, optical fiber bundles, coupled to a remote light source, may be appropriately mounted in body 22 such that light-emitting ends of the bundles are positioned proximate the front face of body 22 in a manner analogous to that of bulbs 28. Two or more bundles, or other light-emitting units, may be positioned about the periphery of body 22 as required to outline the target area.

Referring next to FIGS. 4 through 12, an alternative embodiment of the present invention locates the light-emitting unit within the mouth of the patient. Referring initially to FIG. 4, alignment device 44 of the present invention includes a main body unit 46 adapted to be clenched between the teeth or otherwise properly positioned within the mouth of the patient, and supports one or more light-emitting units 48, as well as a film element 50, in proper position for X-ray exposure.

As may be best seen in FIGS. 5 and 6, the body 46 includes a generally planar film element holder 52 which may be in the form of a channel member as shown, or an equivalent structure adapted to support the film element 50. Mounted to a face 54 of the film holder 52 is support member 56, comprising a base portion 58 affixed to film holder face 54, and projecting teeth-engaging portion 60, having opposed, generally flat faces 62 and 64 against which opposed groups of teeth may bear to retain the body unit in position. Film holder 52 is mounted to support member 56 such that the carried film element 50 is perpendicular to the X-ray path when support member 56 is gripped by the teeth.

Teeth-engaging portion 60 is provided with an aperture or slot 66 extending through front face 68, which is parallel with film element 50 and thus perpendicular to the X-ray path. Light-emitting element 70 is mounted within the aperture 66 such that the beam of emitted light is directed outwardly from front face 68 along the axis of the X-ray beam against and through cheek 72 to form a lighted area 74 on the outer surface of the patient's face. Light-emitting element 70 may be in the form of a miniature light-bulb, pre-focused or otherwise, connected by leads 76 to an external source of power 78, such as a battery pack, having appropriate switching means for the bulb.

Both film element holder 52 and support member 56 are fabricated from appropriate X-ray-transparent materials as known in the art. Support member 56, for example, may be formed of cork or an approved plastic dental casting compound. While bulb 70 and leads 76 are again not X-ray-transparent, the surface area of the film sheet blocked by these elements is not significant and does not adversely affect exposure. In addition, support member 56 may be mounted towards the upper or lower edge of film element holder 52, such that if a particular portion of the mouth is of concern, bulb 70 is not located within the X-ray path to that portion. Alternatively, one or more X-ray transparent elements, such as optical fiber bundles, may be utilized to transmit light generated by a light generating source located in battery pack 78 to the projector unit to further lessen blocking effects that may occur by the use of a bulb as the light-emitting and projecting element.

As may be seen in FIGS. 7 and 8, the body unit 46 may alternatively include a film element holder 80 in a form which encircles film element 50 about only a portion of the element width. In addition to a vertically-oriented aperture 82 for the film element, generally C-shaped film element holder 80 also includes a pair of opposed apertures 84 formed in the opposed faces of the arms 86. These apertures 84 are dimensioned to accept opposed shoulders 88 formed in the support member 90. As film element holder 80 may be formed of a resilient material, support member 90 may be interchangeable, to allow a choice of geometry for the support member as may be required to best position and hold main body unit 46 by the patient's teeth as required.

As shown in FIGS. 9 and 10, both film element holder portion 92 and support member portion 94 of main body unit 46, may alternatively be formed from a unitary piece of resilient material. The unit may be cast with an integral film aperture 82 to allow appropriate positioning of the film element with respect to the support member and the teeth.

As shown in FIGS. 11 and 12, main body unit 46 may also be formed with a film support element 96 in the form of a generally S-shaped bracket dimensioned to engage an edge of the film element 50 between two adjacent arm portions of the bracket. Tubular mounting portion 98 is mounted to the film support element 96, and supports the light-emitting element 70. The light-emitting element 70 may be located in a central tunnel or bore 100, terminating at the front face 102 of tubular portion 98 access to which is provided by connecting slot 104 located in the side wall of the mounting portion body.

It is to be recognized that adaptations and modifications of the invention as disclosed herein may be achieved without departing from the spirit of the invention. The scope of protection sought is thus to be measured by the annexed claims.

I claim:

1. Apparatus for assisting in the positioning of a dental X-ray generating unit for the creation of an X-ray image of an internal target portion of the mouth on a film element, said mouth portion being separated from said X-ray generating unit by a soft-tissue facial portion, comprising a substantially X-ray-transparent body adapted to be mounted in the path of the X-rays within the mouth of the patient and between the X-ray generating unit and the film element, said body having an outwardly-directed face positioned essentially perpendicular to the X-ray path and facing the soft-tissue facial portion between the X-ray source and target and a portion having a pair of opposed surfaces dimensioned to be gripped by the teeth of the patient, and illumination means mounted to said body for directing at least one beam of light perpendicular to and outwardly form said face towards said facial feature along the path of the X-rays generated by the generating unit to produce at least one light spot on said facial feature to serve as an orientation means for said X-ray unit.

2. The apparatus of claim 1, further comprising an X-ray film element support mounted to said body.

3. The apparatus of claim 2, wherein said film element support is formed integrally with said body.

4. The apparatus of claim 1, wherein said illumination means are operatively connected to a power source located outside the patient's mouth.

5. The apparatus of claim 4, wherein said power source comprise a battery.

6. Apparatus for assisting in the positioning of a dental X-ray generating unit for the creation of an X-ray image of an internal target portion of the mouth on a film element, said mouth portion being separated from said X-ray generating unit by a soft-tissue facial portion, comprising a substantially X-ray-transparent body said X-ray generating unit in the path of the X-rays between the X-ray generating unit and the film element, said body having an outwardly-directed face positioned essentially perpendicular to the X-ray path and facing the soft-tissue facial portion between the X-ray source and target, and illumination means mounted about the periphery of said body on said outwardly-directed face for directing at least one beam of light perpendicular to and outwardly from said face towards said facial feature along the path of the X-ray generated by the generating unit to produce at least one light spot on said facial feature to serve as an orientation means for said X-ray unit.

7. The apparatus of claim 6, wherein said illumination means are two in number and are diametrically opposed to each other about said periphery.

8. The apparatus of claim 7, wherein said illumination means comprise electric bulbs.

* * * * *